(12) United States Patent
Natrajan et al.

(10) Patent No.: US 10,759,772 B2
(45) Date of Patent: Sep. 1, 2020

(54) PROCESS FOR THE PREPARATION OF DL-PROLINE CO-CRYSTAL OF DAPAGLIFLOZIN

(71) Applicants: AUROBINDO PHARMA LIMITED, Kondapur, Hitech, Telangana, Hyderabad (IN); Senthilkumar Natrajan, Hyderabad (IN); Kishore Karumanchi, Hyderabad (IN); Vittal Tangirala, Hyderabad (IN); Sivakumaran Meenakshisunderam, Hyderabad (IN)

(72) Inventors: Senthilkumar Natrajan, Hyderabad (IN); Kishore Karumanchi, Hyderabad (IN); Vittal Tangirala, Hyderabad (IN); Sivakumaran Meenakshisunderam, Hyderabad (IN)

(73) Assignee: Aurobindo Pharma Ltd, Hyderabad (IN)

(*) Notice: Subject to any disclaimer, the term of this patent is extended or adjusted under 35 U.S.C. 154(b) by 0 days.

(21) Appl. No.: 16/097,777

(22) PCT Filed: Apr. 28, 2017

(86) PCT No.: PCT/IB2017/052473
§ 371 (c)(1),
(2) Date: Oct. 30, 2018

(87) PCT Pub. No.: WO2017/191539
PCT Pub. Date: Nov. 9, 2017

(65) Prior Publication Data
US 2019/0169152 A1  Jun. 6, 2019

(30) Foreign Application Priority Data

May 2, 2016 (IN) .............................. 201641015162

(51) Int. Cl.
*C07D 309/10* (2006.01)
*C07D 207/12* (2006.01)
*C07C 31/10* (2006.01)
*C07D 207/16* (2006.01)
*C07C 31/20* (2006.01)

(52) U.S. Cl.
CPC ............. *C07D 309/10* (2013.01); *C07C 31/10* (2013.01); *C07C 31/205* (2013.01); *C07D 207/12* (2013.01); *C07D 207/16* (2013.01); *C07B 2200/13* (2013.01)

(58) Field of Classification Search
CPC .. C07D 309/10; C07D 207/12; C07B 2200/13
USPC ........................ 549/417, 423, 418; 548/535
See application file for complete search history.

(56) References Cited

FOREIGN PATENT DOCUMENTS

IN    2014CH01978 A  *  1/2016  ........... C07D 409/10
WO   WO-2008002824 A1  *  1/2008  ............... C07H 7/04

\* cited by examiner

*Primary Examiner* — Matthew P Coughlin
*Assistant Examiner* — Sagar Patel
(74) *Attorney, Agent, or Firm* — Jay R Akhave

(57) ABSTRACT

The present invention relates to a process For the preparation of Dapagliflozin DL-Proline co-crystal and its use in the preparation/purification of Dapagliflozin. The invention also provides a process for the preparation of Dapagliflozin (R,S)-1.2-propanediol monohydrate.

4 Claims, 4 Drawing Sheets

PROCESS FOR THE PREPARATION OF DL-PROLINE CO-CRYSTAL OF DAPAGLIFLOZIN

FIELD OF THE INVENTION

The present invention relates to a process for the preparation of amorphous Dapagliflozin of formula (I). In particular, the present invention relates to a process for the purification of Dapagliflozin.

BACKGROUND OF THE INVENTION

Dapagliflozin is an active sodium-glucose co-transporter-2 (SGLT2) inhibitors and is used in the treatment of patients with type 2 diabetes. Dapagliflozin is chemically known as (2S,3R,4R,5S,6R)-2-[4-chloro-3-(4-ethoxybenzyl)phenyl]-6-(hydroxymethy)tetrahydro-2H-pyran-3,4,5-triol OR (1S)-1,5-anhdro-1-C-[4-chloro-3-[(4-ethoxyphenyl)methyl]phenyl]-D-glucitol, having structural formula as represented by formula (I).

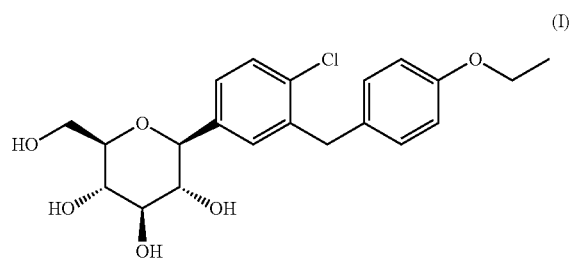 [SMILES: CCOc1ccc(Cc2cc([C@@H]3O[C@H](CO)[C@@H](O)[C@H](O)[C@H]3O)ccc2Cl)cc1]

Dapagliflozin developed by Bristol-Myers Squibb in partnership with AstraZeneca. Dapagliflozin is marketed in USA under the trade name FARXIGA® and Europe as FORXIGA® in the form of tablets having strengths 5 mg and 10 mg. Dapagliflozin inhibits the transporter protein SGLT2 in the kidneys and thereby reduces renal glucose reabsorption, leading to urinary glucose excretion and a reduction in blood glucose levels.

Dapagliflozin and its pharmaceutically acceptable salts first time disclosed in U.S. Pat. No. 6,515,117. US'117 describes the synthesis of Dapagliflozin (as shown in scheme-1 below) using TMS protected gluconolactone and lithium halobenzene as raw materials to provide intermediate as reaction liquid washed with methanol and directly quenched with a solution of methanesulfonic acid to give methoxy Dapagliflozin. This methoxy Dapagliflozin reacted directly with triethylsilane and boron trifluoride to provide crude Dapagliflozin. The purification has carried out by O-acylating the crude Dapagliflozin in pyridine which upon treatment with LiOH provides amorphous Dapagliflozin as a glassy off-white solid with purity 94%.

This crude Dapagliflozin is purified by acetylating crude Dapagliflozin to (1C)-2,3,4,6-tetra-O-acetyl-1,5-anhydro-1-[4-chloro-3-(4-ethoxybenzyl)pheny]-D-glucitol in pyridine.

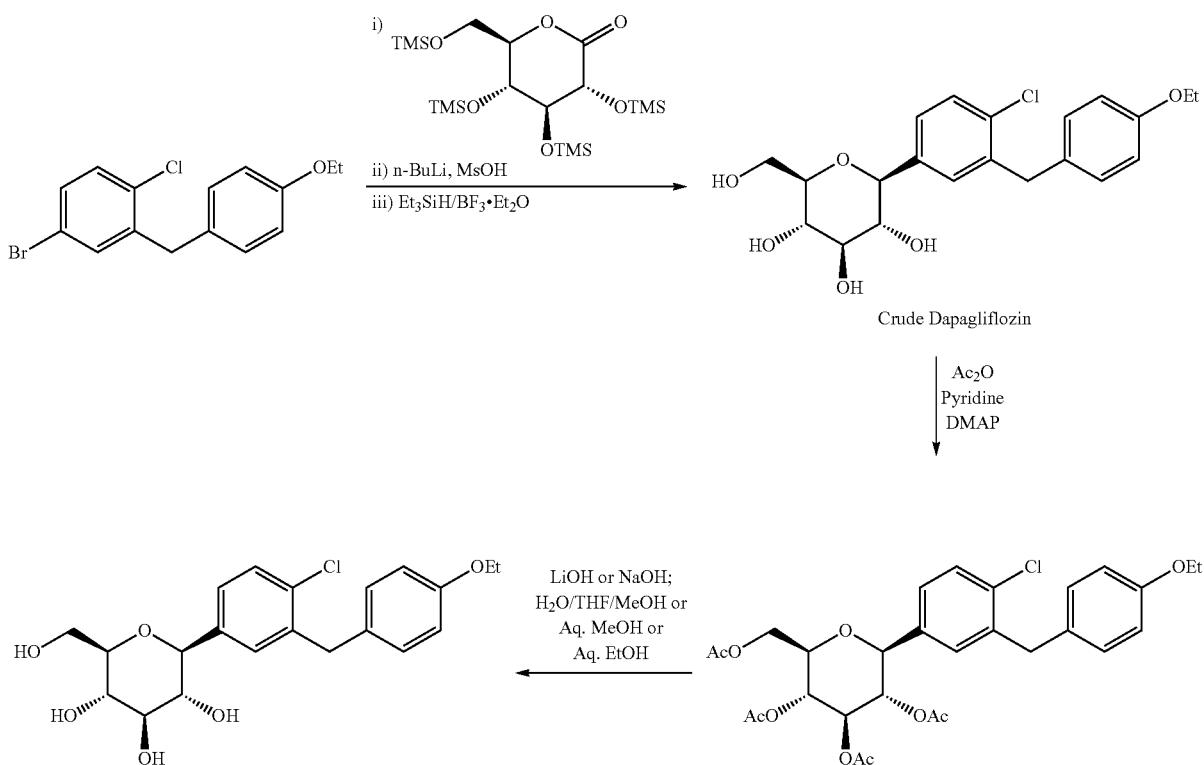

Pyridine is toxic in nature and therefore its use as a solvent should be avoided for industrial production of an active pharmaceutical ingredient. Thus, there is a need in the art to develop a purification process for the preparation of Dapagliflozin that avoids the use of pyridine as a solvent. This method also involves O-acylation of the crude compound which unnecessarily increases the reaction steps, is not conducive to improve the reaction yield and also makes the whole process cumbersome.

U.S. Pat. No. 6,774,112 discloses crystalline complexes of C-aryl glucosides with natural amino acids like (L)-phenylalanine and (L)-proline.

U.S. Pat. No. 7,919,598 (10757/DELNP/2008) discloses 1:2 crystalline complex of L-proline (Form 3), 1:1 crystalline complex of L-proline (Form 6), Hemihydrate of 1:1 crystalline complex of L-proline (Form H5-2), 1:1 crystalline complex of L-phenylalanine (Form 2) and their process.

International Publication No. WO2013/079501A1 describes crystalline Dapagliflozin hydrate Form A and Form B and their processes.

U.S.2015/0307540 discloses amorphous form of Dapagliflozin 1,2-propanediol or hydrates thereof.

Though, there are processes available in the literature for the preparation of amorphous Dapagliflozin, still there remains a need for the production-friendly, stable, cost effective and industrially applicable process for the preparation of pure amorphous Dapagliflozin.

OBJECTIVE

The objective of the present invention relates to a process for the preparation of amorphous form of Dapagliflozin having high chromatographic purity.

Yet another object of the present invention is to provide a process for preparation of Dapagliflozin (RS)-1,2-propanediol monohydrate.

Yet another object of the present invention is to provide a process for preparation of DL-proline co-crystal of Dapagliflozin.

SUMMARY OF THE INVENTION

In this embodiment the present invention provides a process for the preparation of crystalline Dapagliflozin DL-proline co-crystals, comprising:
  a) providing a solution or suspension of Dapagliflozin and DL-proline in a solvent or mixture of solvents;
  b) optionally heating and concentrating the reaction mass; and
  c) isolating Dapagliflozin DL-proline co-crystal.

According to another embodiment, the present invention provides a process for preparation of amorphous Dapagliflozin (I), comprising;
  a) providing a solution of Dapagliflozin DL-proline co-crystal in a solvent or mixture of solvents;
  b) treating the reaction mass obtained in step (a) with a base;
  c) optionally separating the organic layer;
  d) optionally removing the solvent;
  e) adding antisolvent; and
  f) isolating amorphous Dapagliflozin.

According to yet another embodiment, the present invention provides a process for preparation of Dapagliflozin (RS)-1,2-propanediol monohydrate (II), comprising;
  a) providing a solution or suspension of Dapagliflozin and (RS)-1,2-propanediol in a solvent or mixture of solvents;

b) isolating Dapagliflozin (RS)-1,2-propane diol monohydrate.

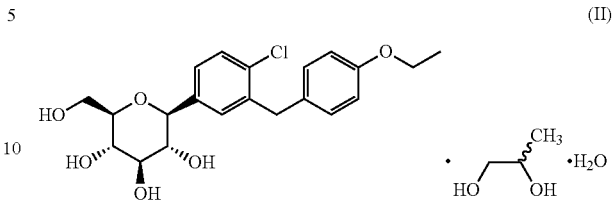

(II)

DETAILED DESCRIPTION OF THE INVENTION

Figure 1:
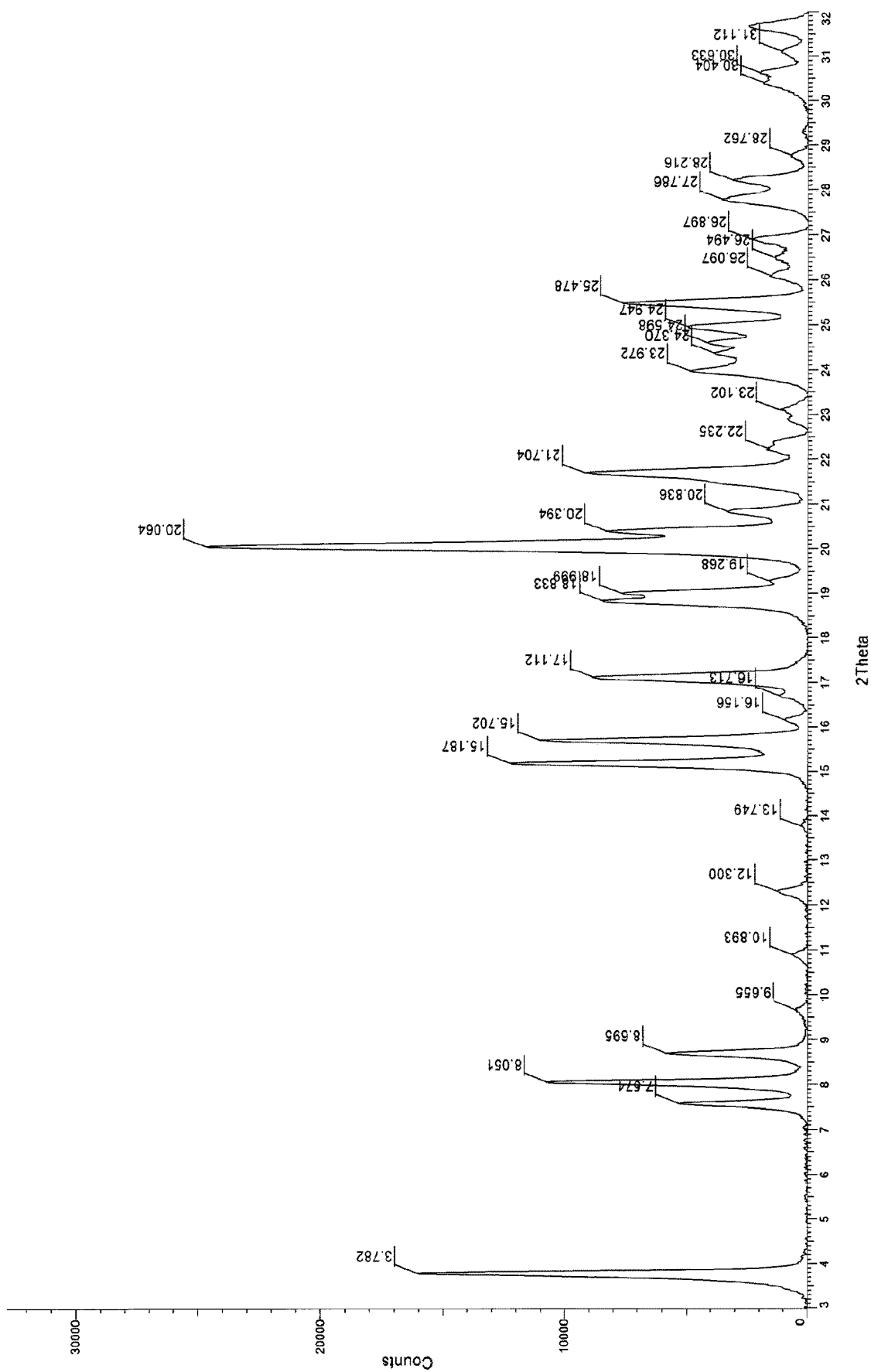
FIG. 1: PXRD pattern of crystalline Dapagliflozin (RS)-1,2-propanediol monohydrate of Formula II prepared according to example 3.
Figure 2:
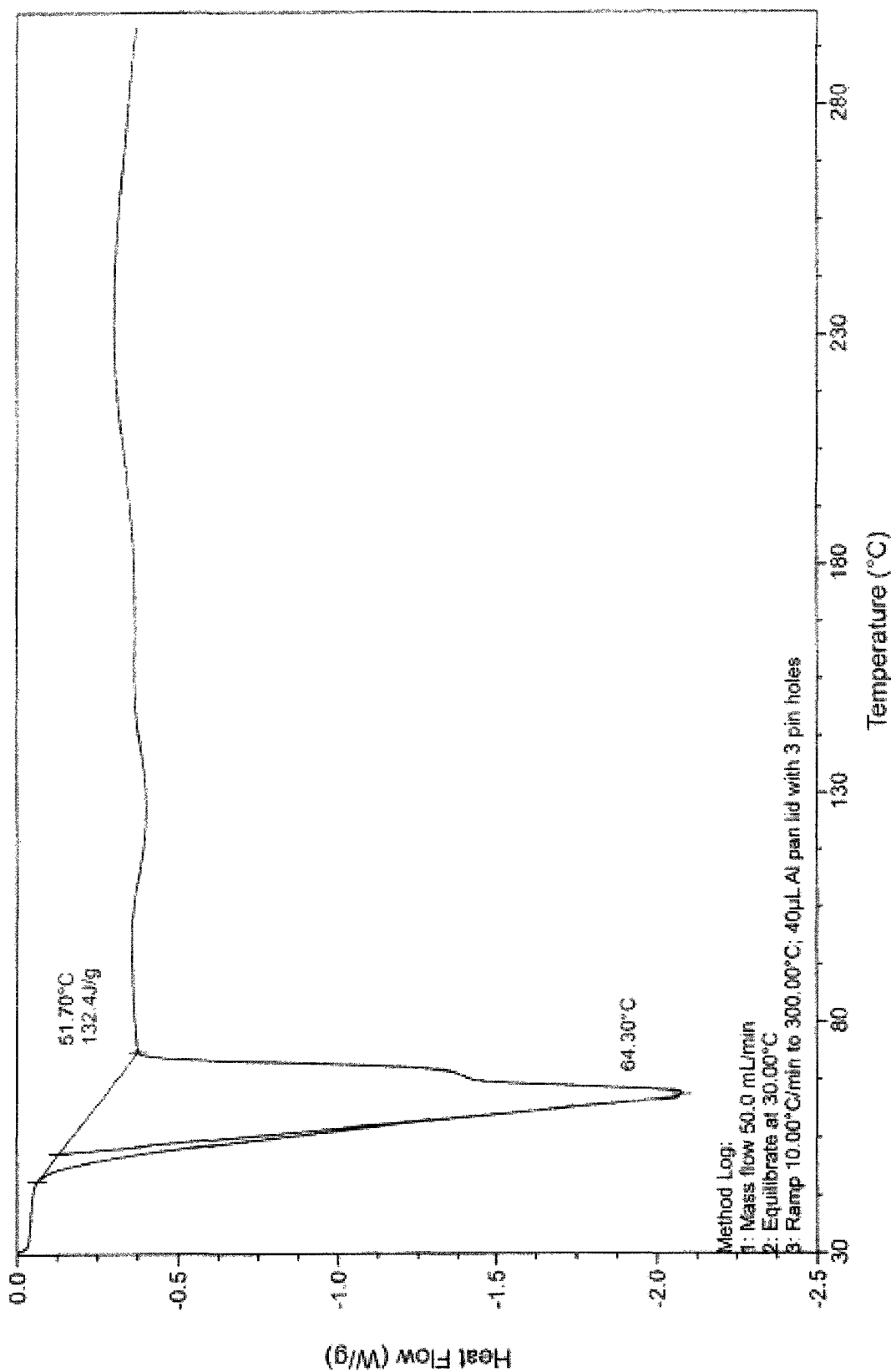
FIG. 2: DSC pattern of crystalline Dapagliflozin (RS)-1,2-propanediol monohydrate of Formula II prepared according to example 3.
Figure 3:
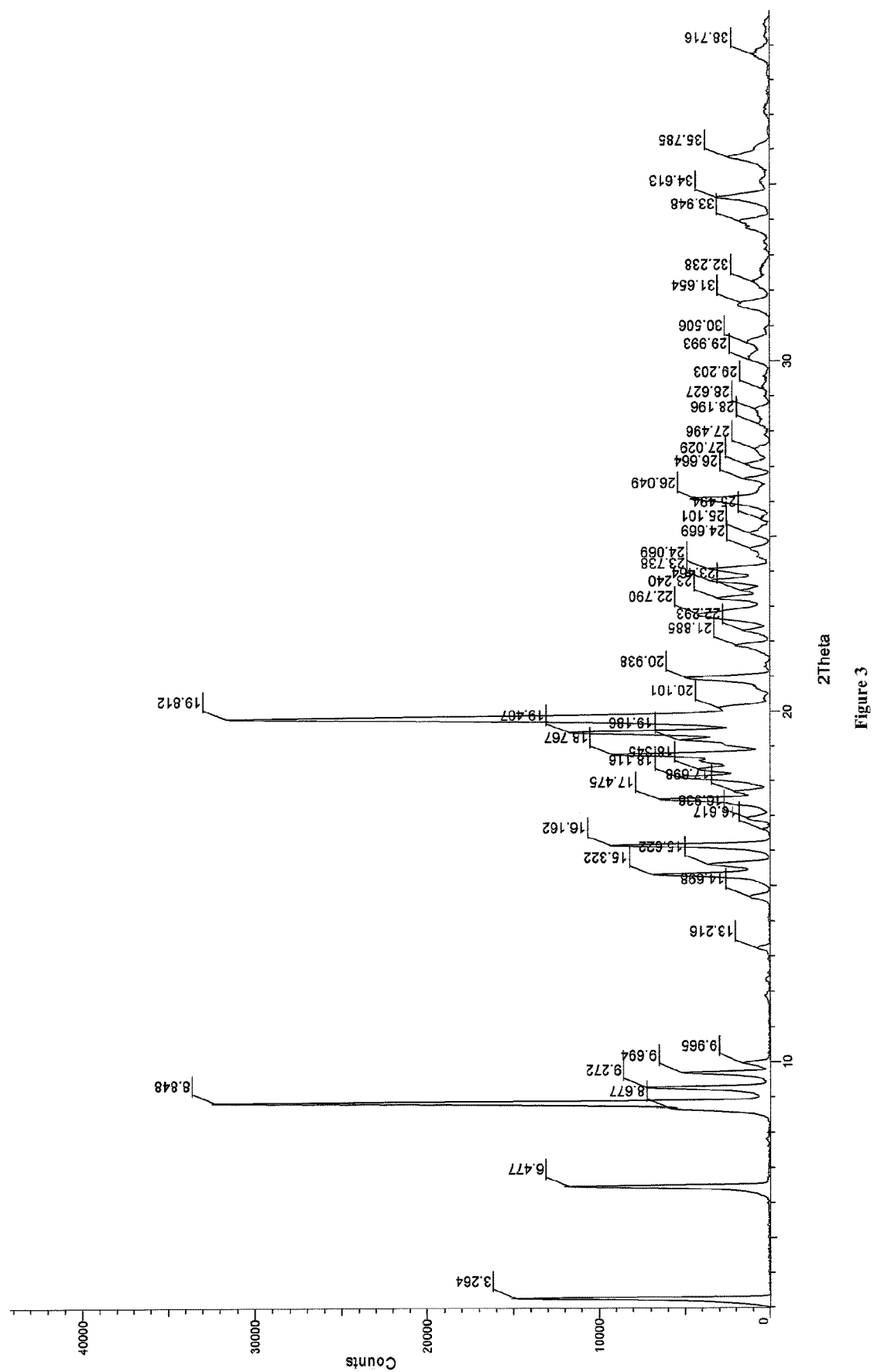
FIG. 3: PXRD pattern of crystalline Dapagliflozin DL-proline co-crystal prepared according to example 5.
Figure 4:
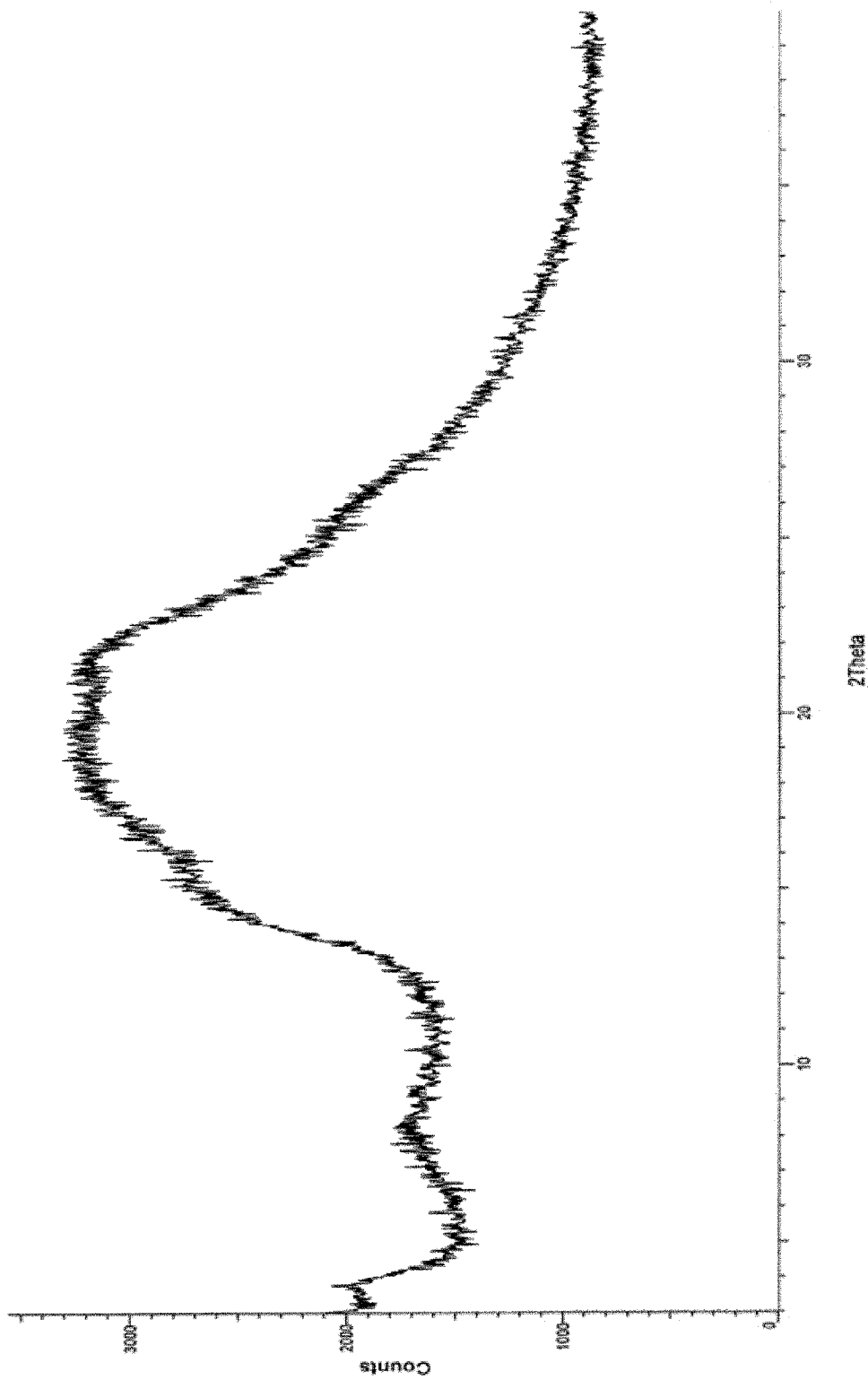
FIG. 4: PXRD pattern of crystalline Dapagliflozin amorphous of Formula I prepared according to example 6.

This invention is directed to a process for the preparation of crystalline Dapagliflozin DL-proline co-crystals, comprising:
  a) providing a solution or suspension of Dapagliflozin and DL-proline in a solvent or mixture of solvents;
  b) optionally heating and concentrating the reaction mass; and
  c) isolating Dapagliflozin DL-proline co-crystals.

In the above invention, if needed optional seeding with co-crystal of Dapagliflozin DL-proline is carried out before the isolation of Dapagliflozin DL-proline co-crystals.

Alternatively the present invention can be carried out using similar racemic amino acids such as alanine, valine, leucine, isoleucine, proline, phenylalanine, tryptophan or methionine, glycine, serine, threonine, cysteine, tyrosine, asparagine, glutamine, lysine, arginine, histidine, aspartic acid or glutamic acid.

The solvent(s) used in step (a) is selected from the group consisting of esters selected from ethyl acetate, and isopropyl acetate; aliphatic hydrocarbons selected from cyclohexane, n-hexane, n-heptane, and pentane; aromatic hydrocarbons selected from toluene, xylene, and naphthalene; halogenated aliphatic hydrocarbons selected from dichloromethane, chloroform, and ethylene dichloride; dialkyl formamides selected from dimethyl formamide; ethers selected from methyl tertiary butyl ether, di-isopropyl ether, di-ethyl ether, dimethyl ether, and methyl butyl ether; cyclic ethers selected from tetrahydrofuran, and 1,4-dioxane; substituted cyclic ethers selected from 2-methyl tetrahydrofuran; alcohols selected from methanol, ethanol, n-propanol, iso-propanol, n-butanol, iso-butanol, n-pentanol, ethylene glycol, and diethylene glycol; ketones selected from acetone, methyl ethyl ketone, and methyl isobutyl ketone; dialkylsulfoxides selected from dimethyl sulfoxide; dialkylacetamides selected from N,N-dimethyl acetamide; nitrites selected from acetonitrile, and propionitrile; ionic liquids, hexamethylphosphorous triamide, hexamethylphosphoramide; water and/or mixtures thereof.

The co-crystal of Dapagliflozin is isolated and dried using conventional methods such as filtration, distillation, evaporation, atmospheric distillation, distillation under vacuum, lyophilization, Freeze drying, spray drying and agitated thin film drying (ATFD) or any other suitable techniques known in the art.

In yet another embodiment of the present invention, crystalline Dapagliflozin DL-proline co-crystals obtained according to the present invention having the Powder X-ray Diffraction (PXRD) °2θ values (±0.2) at 3.26, 6.47, 8.84, 9.27, 15.32, 16.16, 17.47, 18.76, 19.18, 19.4, 19.8 and 20.93. The X-ray diffractogram was measured on Bruker Axe, DS advance Power X-ray Diffractometer with Cu K alpha-1 Radiation source having the wavelength 1.541 A°.

According to another embodiment, the present invention provides a process for preparation of amorphous Dapagliflozin (1), comprising;
  a) providing a solution of Dapagliflozin DL-proline co-crystal in a solvent or mixture of solvents;
  b) treating the reaction mass obtained in step (a) with a base;
  c) optionally separating the organic layer;
  d) optionally removing the solvent;
  e) adding antisolvent; and
  f) isolating amorphous Dapagliflozin.

The solvent(s) used in step (a) is selected from the group consisting of esters selected from ethyl acetate, and isopropyl acetate; ethers selected from methyl tertiary butyl ether, di-isopropyl ether, di-ethyl ether, dimethyl ether, and methyl butyl ether; alcohols such as methanol, ethanol, isopropanol, n-butanol; ketones such as methyl isobutyl ketone, acetone; chlorinated solvents such as methylene chloride; water and/or mixtures thereof.

The base used in step (b) may be organic or inorganic base; the organic bases such as 1,8-diazabicyclo[5.4.0]undec-7-ene; 1,5-diazabicyclo[4.3.0]non-5-ene; primary amines such as methylamine, propyl amine, 2-propyl amine, butyl amine; secondary amines N,N-diisopropyl amine, dimethylamine, diethyl amine, N-methyl propyl amine, morpholine; tertiary amines such as triethylamine, N,N-dimethyl aniline, N,N-diisopropyl ethyl amine, trimethyl amine; pyridine or substituted pyridine such as 2,6-lutidine, 2,4-lutidine, 3,5-lutidine; pyrimidine and N,N-dimethylethyl amine; tetra alkyl ammonium and phosphonium hydroxides; metal alkoxides and inorganic bases such as alkali metal carbonates such as potassium carbonate, sodium carbonate, cesium carbonate; alkali metal bicarbonates such as sodium bicarbonate, potassium bicarbonate; alkali metal hydroxides such as sodium hydroxide, potassium hydroxide, barium hydroxide, lithium hydroxide; metal hydrides; metal alkoxides such as sodium methoxide, sodium ethoxide, potassium tert butoxide; metal amides or liquor ammonia.

The antisolvent used in step (e) is selected from ethers such as methyl tert-butyl ether, diethyl ether, diisopropyl ether, tetrahydrofuran; and hydrocarbons such as hexane, heptane, cyclohexane, and pentane.

According to another embodiment of the present invention the Dapagliflozin co-crystal is a Dapagliflozin DL-proline co-crystal.

According to yet another embodiment, the present invention provides a process for preparation of Dapagliflozin (RS)-1,2-propanediol monohydrate (II), comprising;
  a) providing a solution or suspension of Dapagliflozin and (RS)-1,2-propane diol in a solvent or mixture of solvents;
  b) isolating Dapagliflozin (RS)-1,2-propane diol monohydrate.

The solvent(s) used in step (a) is selected from the group consisting of esters selected from ethyl acetate, and isopropyl acetate; aliphatic hydrocarbons selected from cyclohexane, n-hexane, n-heptane, and pentane; aromatic hydrocarbons selected from toluene, xylene, and naphthalene; halogenated aliphatic hydrocarbons selected from dichloromethane, chloroform, and ethylene dichloride; dialkyl formamides selected from dimethyl formamide; ethers selected from methyl tertiary butyl ether, di-isopropyl ether, di-ethyl ether, dimethyl ether, and methyl butyl ether; cyclic ethers selected from tetrahydrofuran, and 1,4-dioxane; substituted cyclic ethers selected from 2-methyl tetrahydrofuran; alcohols selected from methanol, ethanol, n-propanol, iso-propanol, n-butanol, iso-butanol, n-pentanol, ethylene glycol, and diethylene glycol; ketones selected from acetone, methyl ethyl ketone, and methyl isobutyl ketone; dialkylsulfoxides selected from dimethyl sulfoxide; dialkylacetamides selected from N,N, -dimethyl acetamide; nitrites selected from acetonitrile, and propionitrile; ionic liquids, hexamethylphosphorous triamide, hexamethylphosphoramide; water and/or mixtures thereof.

The Dapagliflozin (RS)-1,2-propanediol monohydrate is isolated and dried using conventional methods such as filtration, distillation, evaporation, atmospheric distillation, distillation under vacuum, lyophilization, Freeze drying, spray drying and agitated thin film drying (ATFD) or any other suitable techniques known in the art.

Dapagliflozin used in the present invention may be prepared according to process disclosed in the U.S. Pat. No. 6,515,117 or any known method in the prior-art.

A co-crystal of this invention is a molecular complex with a crystalline structure composed of at least two components, wherein the components may be atoms, ions or molecules.

The purity of amorphous form of Dapagliflozin prepared according to the present invention is greater than 98%, preferably greater than 99% and more preferably 99.5% by HPLC. Thus the present invention achieves the purity without using column chromatography and provides industrially viable robust process for the preparation of amorphous form of Dapagliflozin. Surprisingly it has been found that the amorphous form prepared according to the present invention posses better stability over the prior art process and does not convert to any other form under stressed condition. Thus the present invention provides an industrially scalable process for the preparation of amorphous form of Dapagliflozin with high purity and stability with consistent yields.

The invention is illustrated with the following examples, which are provided by way of illustration only and should not be construed to limit the scope of the invention in any manner whatsoever.

EXAMPLES

Reference Example 1

Preparation of Methoxy Dapagliflozin

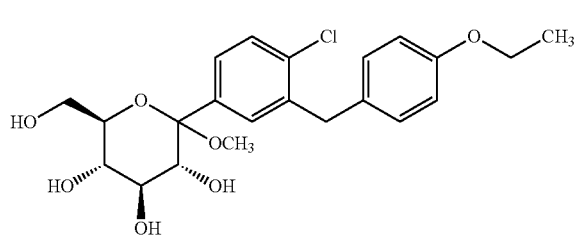 [SMILES: CCOc1ccc(Cc2cc(C3(OC)O[C@H](CO)[C@@H](O)[C@H](O)[C@H]3O)ccc2Cl)cc1]

5-Bromo-2-chloro-4'-ethoxy-diphenylmethane (125 g) was dissolved in a mixture of THF and toluene and cooled to −75° C. N-butyl lithium (195 ml, 1.2 eq.) was added slowly to the reaction mass at −70 to −75° C. The reaction mass was stirred at −70 to −75° C. Separately, 2,3,4,6-tetra-O-trimethylsilyl-β-D-glucolactone [TMS glucolactone] (197 g) was dissolved in toluene and cooled to −50° C. The pre-cooled TMS glucolactone solution was added to above reaction mass at −70 to −75° C. and stirred at −70 to −75° C. The reaction mass was quenched by addition of methanesulfonic acid solution [prepared by dissolving methanesulfonic acid (97 g) in methanol]. The reaction mass was slowly warmed to 20-25° C. and stirred. The reaction mass was neutralized with aqueous sodium bicarbonate to pH 7.3 and separated the organic layer. The aqueous layer was extracted with toluene. Both the organic layers were combined and washed with aqueous sodium chloride solution. The resulting solution was concentrated at 40-45° C. under vacuum. The residue was dissolved in hot toluene, poured into cyclohexane under vigorous stirring. The product was filtered, washed with cyclohexane and dried under vacuum to yield methoxy Dapagliflozin.
Yield: 137 g.

Reference Example 2

Preparation of (Dapagliflozin Crude (I)

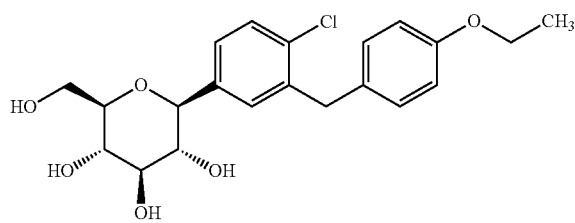 [SMILES: CCOc1ccc(Cc2cc([C@@H]3O[C@H](CO)[C@@H](O)[C@H](O)[C@H]3O)ccc2Cl)cc1]

Methoxy Dapagliflozin (135 g) was dissolved in methylene chloride and cooled to −45 to −50° C. Triethyl silane (143.2 g) was added at −45° C. followed by borontrifluoride etherate (131.3 g). The reaction mass was slowly warmed to −10 to −5° C. and stirred. The reaction mass was neutralized with aqueous sodium bicarbonate solution. The organic layer was separated. The aqueous layer was extracted with ethyl acetate. The total organic layer was washed with DM water. The resulting organic layer was concentrated at 40° C. under vacuum to yield Dapagliflozin (crude).
Yield: 130 g.

Example 1

Preparation of Methoxy Dapagliflozin

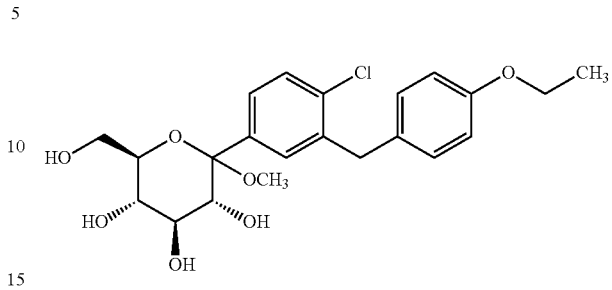

5-Bromo-2-chloro-4'-ethoxydiphenylmethane (150 g) was dissolved in a mixture of THF and toluene and cooled to −85° C. n-butyl lithium solution in hexanes (195 ml, 1.2 eq.) was added slowly to the reaction mass at −85° C. to −75° C. The reaction mass was stirred at −85° C. to −75° C. for 30 min. 2,3,4,6-tetra-O-trimethylsilyl-β-D-glucolactone [TMS glucolactone] (197 g) was dissolved in toluene and added to the above solution at −85° C. to −75° C. The reaction mass was stirred for 1 h at −85° C. to −75° C. A solution of methanesulfonic acid (88.6 g) in methanol (900 ml) was slowly added to the reaction mass at −85° C. to −75° C. The reaction mass was slowly warmed to 20-30° C. and stirred for 2 h. 7% aqueous sodium bicarbonate was added to the above reaction mass at 20-30° C. and separated the organic layer. The aqueous layer was extracted with ethyl acetate (2×900 ml). The combined organic layer was washed with aqueous sodium chloride solution. The resulting solution was concentrated at below 60° C. under vacuum upto a volume of 500 ml and added to cyclohexane (3000 ml). The precipitated product was filtered, washed with cyclohexane and dried under vacuum to yield methoxy Dapagliflozin.
Yield: 150 g.

Example 2

Preparation of Dapagliflozin DL-Proline Co-Crystal [1:2]

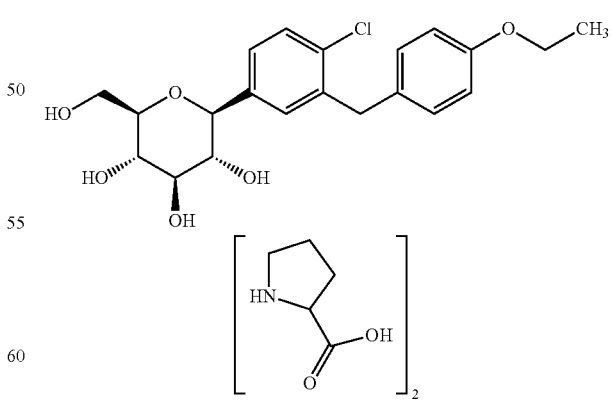

Dapagliflozin (130 g) was dissolved in isopropyl alcohol at 25-30° C. DL-proline (88.6 g) and DM water was added at 25-30° C. The reaction mass was heated to reflux and stirred. The reaction mass was concentrated completely at 50° C.

under reduced pressure. To the resulting residue, isopropyl alcohol was added and stirred at 20-30° C. The product was filtered and washed with isopropyl alcohol. The wet product was slurried in isopropyl alcohol, filtered, washed with isopropyl alcohol and dried to yield Dapagliflozin DL-proline co-crystals.

Yield: 152.8 g; Purity (by HPLC): >99.9%.

Example—3

Preparation of Amorphous Dapagliflozin (I)

Dapagliflozin DL-proline (100 g) was added to ethyl acetate and DM water at 25-30° C. Aqueous sodium carbonate (16.6 g in 166 ml of DM water) was added and stirred. The organic layer was separated and washed with DM water. The organic layer was concentrated at 40° C. under vacuum. The resulting residue was dissolved in MTBE at 25-30° C. and added to cyclohexane at 25-30° C. The precipitated product was filtered, washed with cyclohexane under nitrogen and dried to yield Dapagliflozin amorphous.

Yield: 45 g; Purity (by HPLC): >99.9%.

Example—4

Preparation of Dapagliflozin (RS)-1,2-Propanediol Monohydrate

Dapagliflozin (6 g) was dissolved in isopropyl acetate (35 ml) at 25-30° C. (RS)-1,2-propanediol and water (0.26 ml) was added and stirred for 1 h. cyclohexane (52 ml) was added and stirred for 30 min at 25-30° C. The slurry was cooled to 0-5° C. and stirred for 1 h. The product was filtered and washed with cyclohexane (20 ml). The wet product was dried to yield Dapagliflozin (RS)-1,2-propanediol monohydrate.

Yield: 6 g; Purity (by HPLC): >99.9%.

Example—5

Preparation of Dapagliflozin DL-Proline Co-Crystal [1:4]

Methoxy dapagliflozin (150 g) was dissolved in methylene chloride (900 ml) at 20-30° C. and cooled to −40° C. to −45° C. Triethylsilane (105.3 g) was added at −40° C. to −45° C. Borontrifluoride etherate (129 g) was added at −40° C. to −45° C. The reaction mass was slowly warmed to −10 to −5° C. and stirred for 1 h. Further the temperature was increased to −5° C. to 0° C. and continued stirring for 1 h. The reaction mass was neutralized with aqueous sodium bicarbonate solution. Methylene chloride was distilled out from the reaction mass at 40° C. under reduced pressure. To the resulting suspension, ethyl acetate (1500 ml) was added and stirred for 30 min. Separate the organic layer and was washed with DM water (400 ml) and concentrated at 40° C. under reduced pressure. The resulting oily mass was dissolved in isopropanol (750 ml) at 40-45° C. Separately, DL-proline (157.5 g) was added to DM water (50 ml) and isopropanol (300 ml) at 25-30° C. and heated to reflux. The above isopropanol solution of dapagliflozin was added to DL-proline solution at reflux. The resulting solution was cooled to 20-30° C. and stirred for about 10 h. Further the precipitated product was cooled to 0-5° C. and stirred for 2 h. The product was filtered and washed with precooled isopropyl alcohol (300 nil) and dried to yield dapagliflozin DL-proline (260 g).

Yield: 260 g; Purity (by HPLC): >99.9%.

Example—6

Preparation of Amorphous Dapagliflozin (I)

Dapagliflozin DL-proline (200 g) was added to DM water (2000 ml) at 20-30° C. Aqueous sodium carbonate (266 ml) was added and stirred for 1 h. Methyl tert-butyl ether (MTBE) (2000 ml) was added to the above reaction mass and stirred for 30 min. The organic layer was separated and washed with DM water (1000 ml). The resulting organic layer was heated to reflux at 50-60° C. and simultaneously water was removed through Dean-Stark apparatus by distilling water-methyl tert butyl ether azeotrope till water content of methyl tert butyl ether solution is less than 0.1%.

Separately, n-Heptane (4000 ml) was cooled to 15-20° C. and added the above hot methyl tert butyl ether solution. The precipitated product was filtered and washed with n-Heptane (100 ml). The wet product was dried under reduced pressure for about 15 h. Further, the product was dried at 48-52° C. under reduced pressure for 10 h to meet ICH limit of residual Methyl tert-butyl ether (MTBE) and n-Heptane to yield Dapagliflozin amorphous.

Yield: 80 g; Purity (by HPLC): >99.9%.

We claim:

1. A process for preparation of amorphous Dapagliflozin (I), comprising the steps of:
   a) providing a solution of Dapagliflozin DL-proline co-crystal in a solvent or mixture of solvents;
   b) treating the reaction mass obtained in step (a) with a base;
   c) optionally separating the organic layer;
   d) optionally removing the solvent;
   e) adding antisolvent; and
   f) isolating amorphous Dapagliflozin.

2. The process according to claim 1, wherein the solvent used in step (a) is selected from the group consisting of ethyl acetate, isopropyl acetate, methyl tertiary butyl ether, di-isopropyl ether, di-ethyl ether, dimethyl ether methyl butyl ether, methanol, ethanol, isopropanol, n-butanol, methyl isobutyl ketone, acetone, methylene chloride, and water, or mixtures thereof.

3. The process according to claim 1, wherein the base used in step (b) may be organic or inorganic base; the organic base selected from the group consisting of 1,8-diazabicyclo[5.4.0]undec-7-, 1,5-diazabicyclo [4.3.0]non-5-ene, methylamine, propylamine, 2-propyl amine, butyl amine, N-diisopropyl amine, dimethylamine, diethylamine, N-methyl propyl amine, morpholine, triethylamine, N,N-dimethyl aniline, N,N-diisopropyl ethyl amine, trimethyl amine, pyridine, 2,6 lutidine, 2,4-lutidine, 3,5-ludtidine, pyrimidine, N,N-dimethylelethyl, amine,-tetra alkyl ammonium, phosphonium hydroxides, and metal alkoxides; and inorganic base selected from the group consisting of potassium carbonate, sodium carbonate, cesium carbonate, sodium bicarbonate, potassium bicarbonate; sodium hydroxide, potassium hydroxide, barium hydroxide, lithium hydroxide, metal hydrides, sodium methoxide, sodium ethoxide, potassium tert butoxide, metal amides, and liquor ammonia.

4. The process according to claim 1, wherein the antisolvent used in step (e) is selected from group consisting of hexane, heptane, cyclohexane; and pentane.

* * * * *